(12) United States Patent
Houde et al.

(10) Patent No.: US 7,326,224 B2
(45) Date of Patent: Feb. 5, 2008

(54) SHAFT AND WIRE LOCK

(75) Inventors: Eric Houde, Saratoga Springs, NY (US); Colin P. Hart, Queensbury, NY (US); Mark H. Van Diver, Argyle, NY (US); Thomas Deyette, Jr., Hudson Falls, NY (US); Scott A. Diamond, Fort Edward, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 654 days.

(21) Appl. No.: 10/167,341

(22) Filed: Jun. 11, 2002

(65) Prior Publication Data

US 2003/0229295 A1    Dec. 11, 2003

(51) Int. Cl.
*A61F 2/01* (2006.01)
(52) U.S. Cl. ...................................... 606/200
(58) Field of Classification Search .............. 606/200, 606/198; 604/103.03, 103.04
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,832,055 A | 5/1989 | Palestrant | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,998,539 A | 3/1991 | Delsanti | |
| 5,002,560 A | 3/1991 | Machold et al. | |

(Continued)

FOREIGN PATENT DOCUMENTS

| | | |
|---|---|---|
| DE | 28 21 048 | 7/1980 |
| DE | 34 17 738 | 11/1985 |
| DE | 40 30 998 A1 | 10/1990 |
| DE | 199 16 162 | 10/2000 |

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).
"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).

(Continued)

*Primary Examiner*—Michael Thaler
(74) *Attorney, Agent, or Firm*—Crompton, Seager & Tufte LLC

(57) ABSTRACT

The present invention relates generally to the field of embolic protection and, more particularly, to systems for locking a shaft relative to a hub assembly. In addition, a method for securing a shaft relative to a hub assembly is disclosed.

28 Claims, 9 Drawing Sheets

U.S. PATENT DOCUMENTS

| | | |
|---|---|---|
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,068,158 A | 5/2000 | Engelson et al. |
| 6,068,645 A | 5/2000 | Tu |
| 6,086,605 A | 7/2000 | Barbut et al. |
| 6,096,009 A | 8/2000 | Windheuser et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,620,148 B1 * | 9/2003 | Tsugita .................... 604/509 |
| 2001/0041908 A1 | 11/2001 | Levinson et al. |
| 2002/0026149 A1 | 2/2002 | Agro et al. |
| 2002/0026211 A1 | 2/2002 | Khosravi et al. |
| 2002/0128678 A1 | 9/2002 | Petersen |

FOREIGN PATENT DOCUMENTS

| | | |
|---|---|---|
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |

| | | |
|---|---|---|
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Recognition and Embolic Potential of Intraaortic Atherosclerotic Debris," American College of Cardiology (Jan. 1991).

Cragg, Andrew et al., " A New Percutaneous Vena Cava Filger," *AJR*, 141:601-604 (Sep. 1983).

Cragg, Andrew et al., "Nonsurgical Placement of Arterial Endoprothesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2): English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

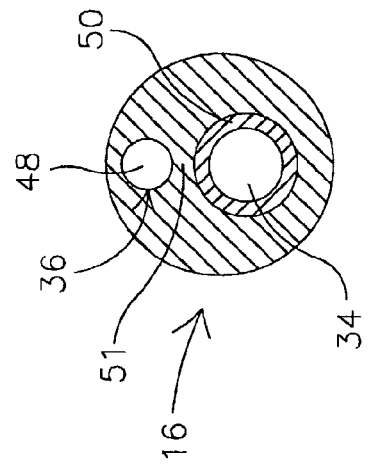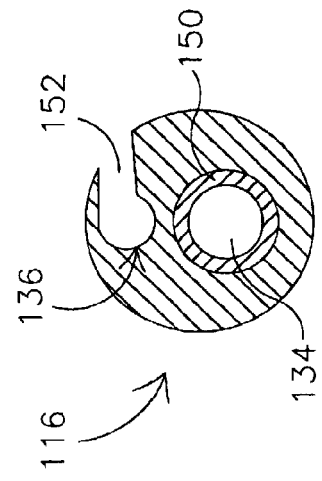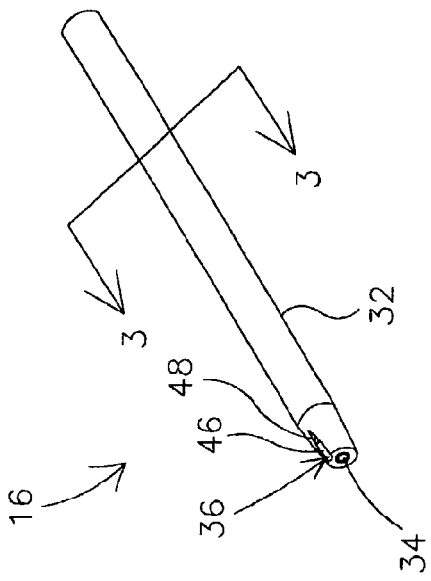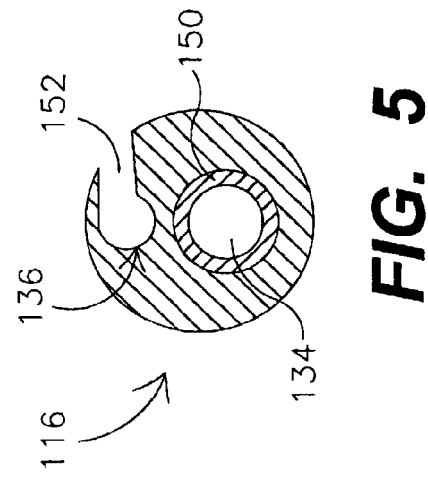

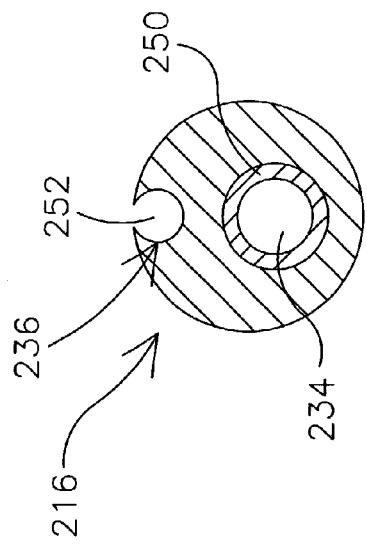
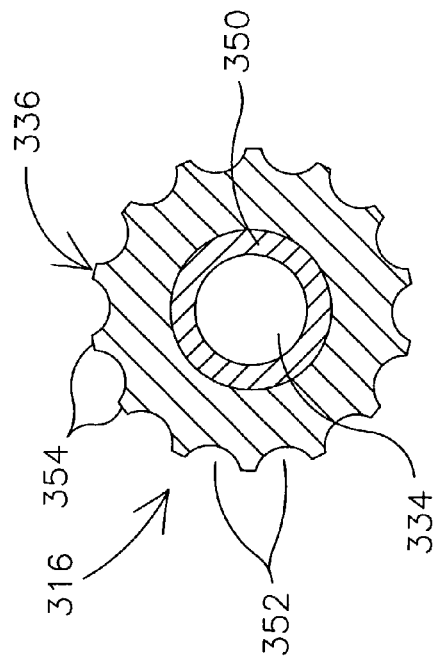
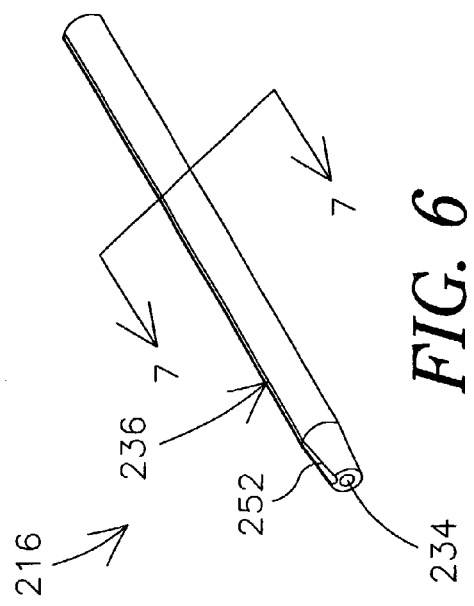
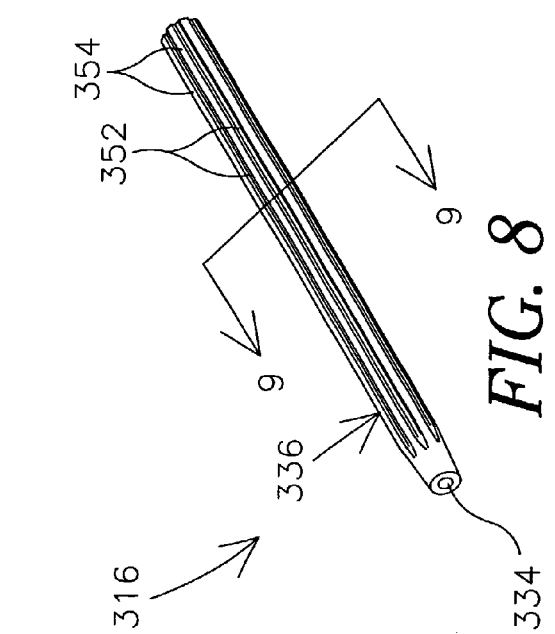
FIG. 6
FIG. 7
FIG. 8
FIG. 9

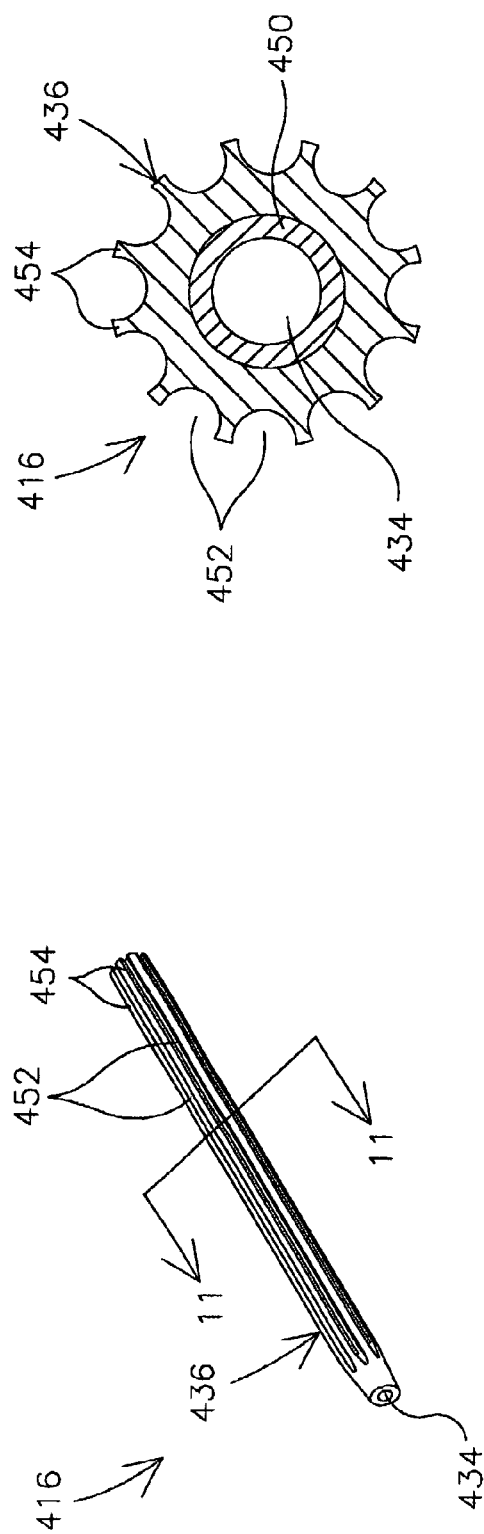
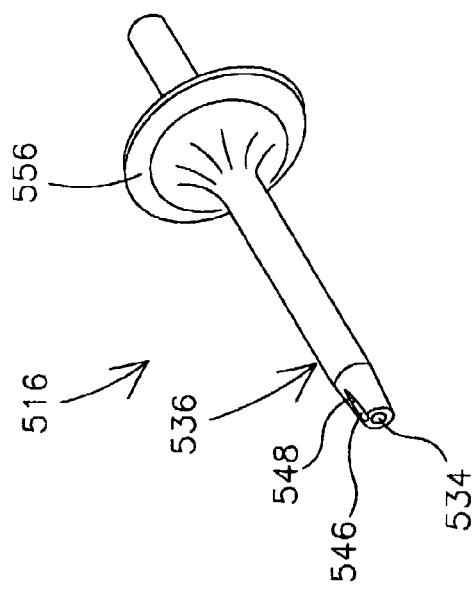
FIG. 11
FIG. 10
FIG. 12

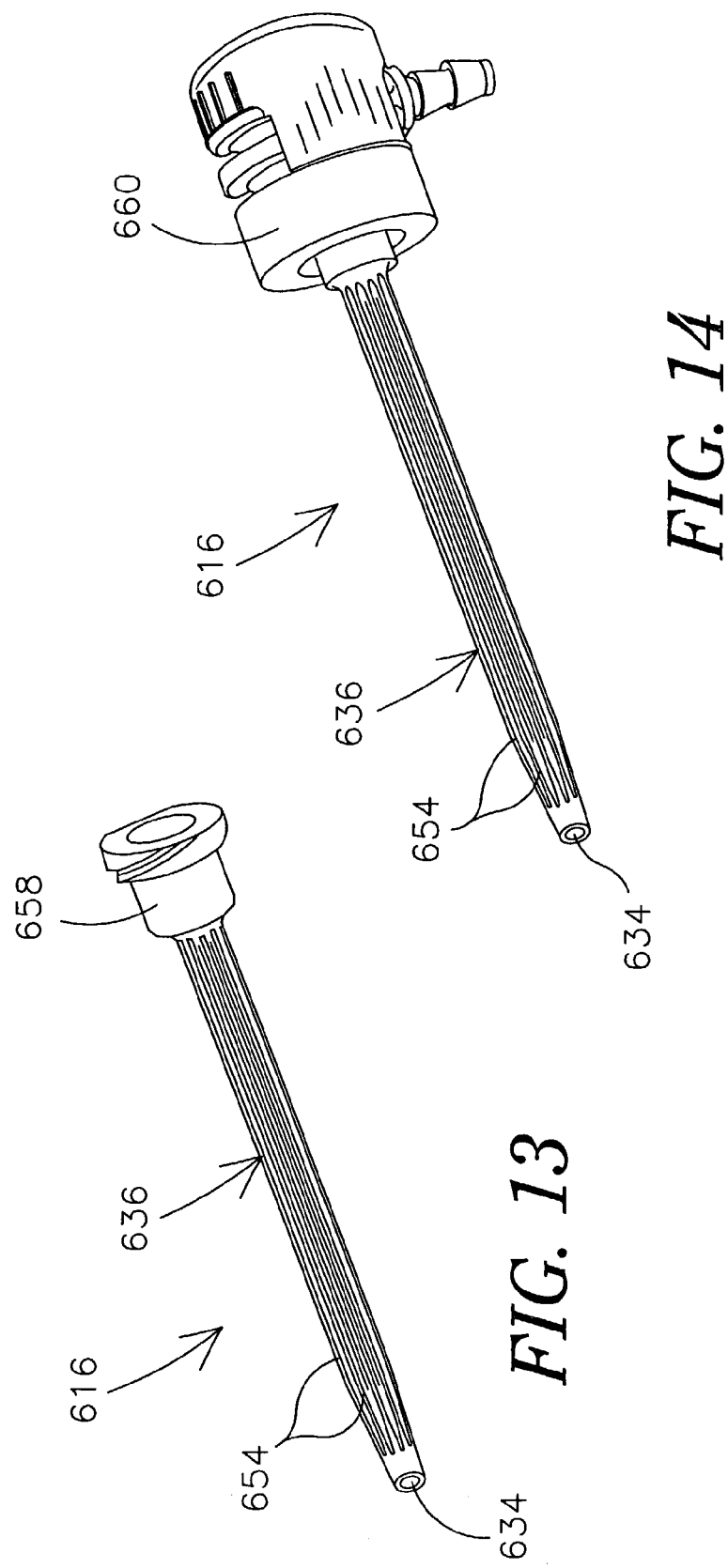

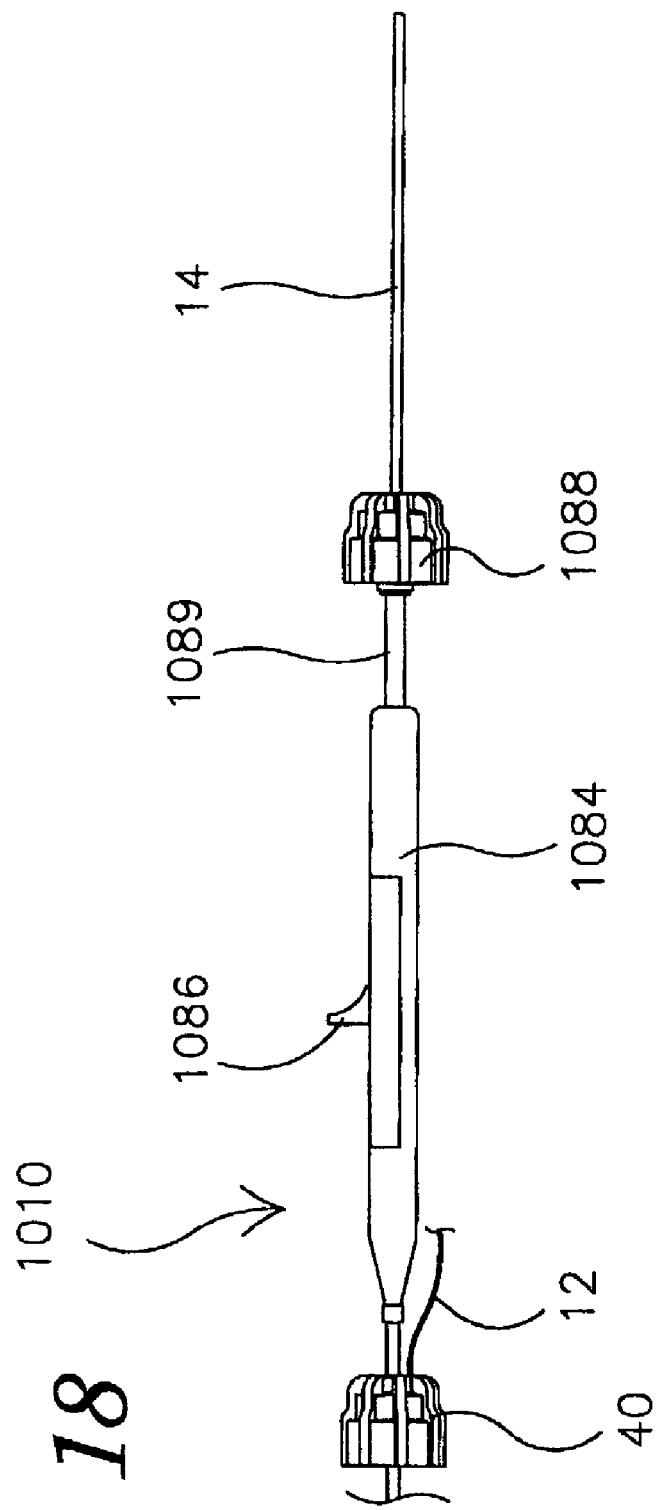

SHAFT AND WIRE LOCK

FIELD OF THE INVENTION

The present invention relates generally to the field of embolic protection. More particularly, the present invention pertains to systems for locking a filter shaft relative to a delivery or retrieval sheath in an embolic protection device.

BACKGROUND OF THE INVENTION

Heart disease is a major problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned within a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature, both of which are highly undesirable. During angioplasty procedures, stenotic debris may also break loose due to manipulation of the blood vessel. Because of this debris, a number of devices, termed embolic protection devices, have been developed to filter out this debris.

SUMMARY OF THE INVENTION

The present invention pertains to embolic protection devices. More particularly, the present invention includes a system for locking a shaft relative to a delivery or retrieval sheath. The sheath may comprise a proximal end, a distal end, and a lumen extending therethrough. The shaft may have an embolic protection filter coupled to its distal end. The shaft may be adapted to be disposed within the lumen of the sheath.

An assembly may be coupled to the sheath and a splitter may be coupled to the assembly. The splitter may include a tube having an inner lumen adapted to slidably receive the sheath, and a shaft coupling portion to secure the shaft relative to the assembly with a locking member. Multiple differing embodiment of the splitters are disclosed. For example, the shaft coupling portion may include a wire lumen. Alternatively, the shaft coupling portion may include a slot. The shaft may be secured relative to the assembly by a collet, a collar, a slot, a pinchable tube, etc. The splitter may further comprise a physical stop or a luer adapter.

Alternate embodiments of the present invention may also include a sliding handle or the inclusion of a securement shaft. These embodiments may help to address the issue of catheter bowing, which may also interfere with movement of the shaft relative to the assembly.

BRIEF DESCRIPTION OF THE DRAWINGS

FIG. 2 is a perspective view of a splitter for use with the shaft and sheath lock system;

FIG. 3 is a cross-sectional view through line 3-3 of the splitter shown in FIG. 2;

FIG. 4 is a perspective view of an alternate splitter for use with the shaft and sheath lock system;

FIG. 5 is a cross-sectional view through line 5-5 of the splitter shown in FIG. 4;

FIG. 6 is a perspective view of a second alternate splitter for use with the shaft and sheath lock system;

FIG. 7 is a cross-sectional view through line 7-7 of the splitter shown in FIG. 6;

FIG. 8 is a perspective view of a third alternate splitter for use with the shaft and sheath lock system;

FIG. 9 is a cross-sectional view through line 9-9 of the splitter shown in FIG. 8;

FIG. 10 is a perspective view of a fourth alternate splitter for use with the shaft and sheath lock system;

FIG. 11 is a cross-sectional view through line 11-11 of the splitter shown in FIG. 10;

FIG. 12 is a perspective view of a fifth alternative splitter having a physical stop;

FIG. 13 is a perspective view of a sixth alternative splitter having a luer adapter;

FIG. 14 is a perspective view of the splitter shown in FIG. 13 further comprising a passive valve coupled to the luer adapter;

FIG. 18 is a side view of an alternate embolic protection assembly; and

DETAILED DESCRIPTION

Figure 1:
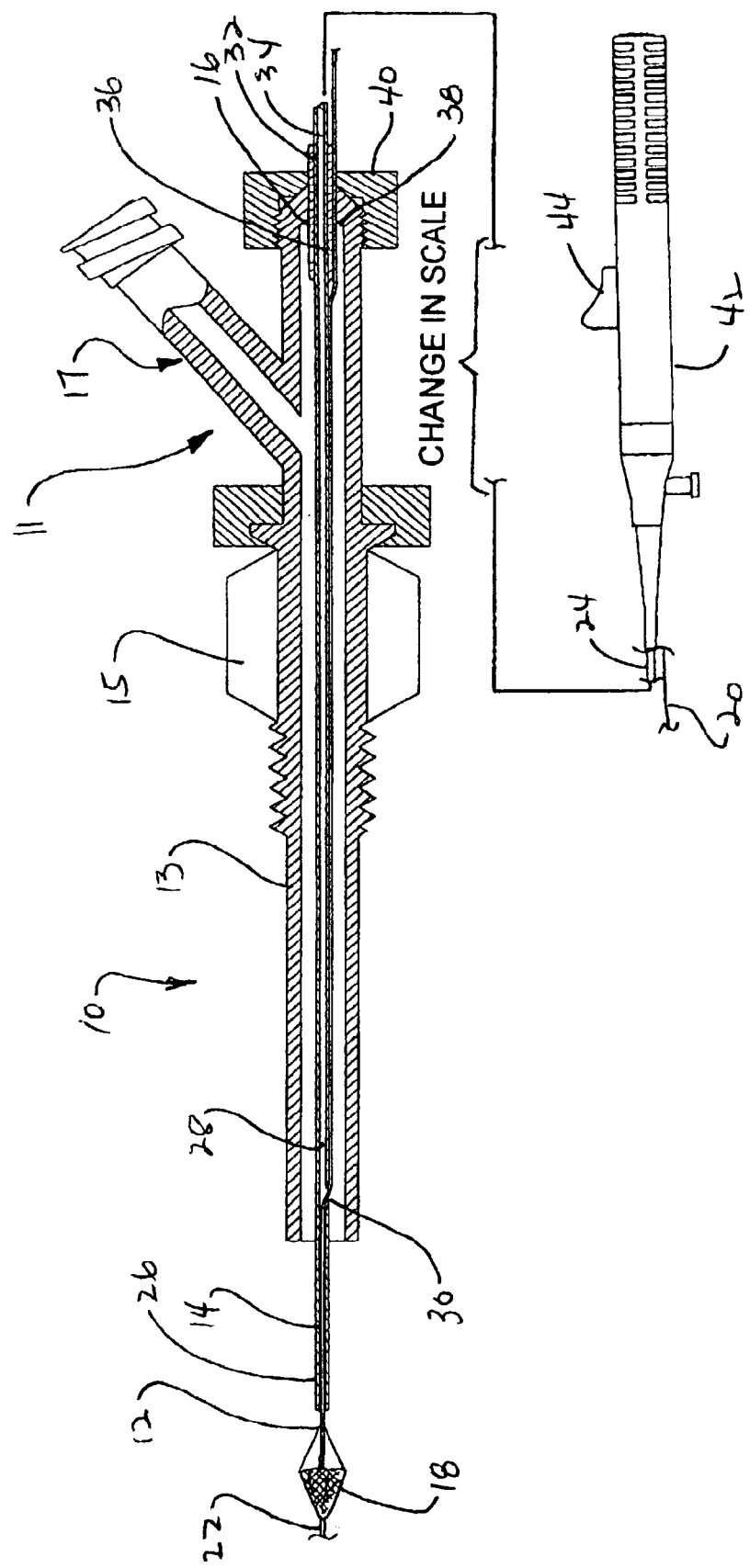
FIG. 1 is a partial cross-sectional view of an embolic protection assembly including a system for locking an elongate shaft relative to a hub assembly.

The following description should be read with reference to the drawings wherein like reference numerals indicate like elements throughout the several views. The detailed description and drawings illustrate example embodiments of the claimed invention.

When delivering or retrieving an embolic protection filter, it may be important to the secure the position of the filter relative to a delivery or retrieval sheath. This may allow a clinician to accurately deliver or retrieve the filter and minimize unwanted or unplanned movement. FIG. 1 is a partial cross-sectional view of an embolic protection assembly 10 including a shaft and sheath lock system 11 for locking an elongate shaft or wire 12 relative to a sheath 14. Shaft and sheath lock system 11 may include a splitter 16 that may separately couple to both shaft 12 and sheath 14 to, for example, secure shaft 12 while allowing movement of sheath 14. The inclusion of splitter 16 may allow the clinician to easily and precisely deliver or retrieve an embolic protection filter 18.

Assembly 10 may include a hub and/or guide catheter assembly including, for example, a guide catheter 13 with a proximal hub 15 having a y-adaptor 17 attached thereto. The configurations of guide catheter 13, hub 15 and y-adaptor 17 can be similar to similar devices known in the art. Guide catheter 13, hub 15, and y-adaptor 17 may all be configured to receive sheath 14 within an inner lumen.

Shaft 12 may comprise a guidewire having a proximal end 20 and a distal end 22. Shaft 12 may be comprised of metals including, but not limited to stainless steel, nickel alloys, and nickel-titanium alloys. Alternatively, shaft 12 may be comprised of one or more polymers or a metal-polymer composite. Embolic protection filter 18 may be coupled to shaft 12 proximate distal end 22.

Filter 18 may be comprised of a polyurethane sheet and include at least one opening that may be, for example, formed by known laser techniques. The holes or openings are sized to allow blood flow therethrough but restrict flow of debris or emboli floating in the body lumen or cavity. Filter 18 may be generally cone-shaped, and have a proximal and a distal end. The distal end may be a narrow, "V"-shaped end and can be fixedly secured or formed to shaft 12. The proximal end has a relatively wide opening.

Filter 18 operates between a closed collapsed profile and an open radially-expanded deployed profile for collecting debris in a body lumen. Filter 18 may include a collapsible proximally-tapered frame having a mouth and a plurality of longitudinally-extending ribs. In an expanded profile, the mouth is opened and the ribs extend radially outwardly to support the mouth. A number of differing configurations of filter 18 may be substituted without departing from the spirit of the invention.

Sheath 14 may be comprised of one or more metals (such as those listed above), one or more polymers, or a metal-polymer composite. Sheath 14 may be generally tubular and include a proximal end 24, a distal end 26, and a lumen 28 extending through at least a portion thereof that is adapted and configured to slidably receive shaft 12. For example, lumen 28 may extend through a portion of sheath 14 and exit sheath 14 through a port 30 located near distal end 26 so that sheath 14 may be used in combination with shaft 12 as a single-operator-exchange catheter. Alternatively, lumen 28 could extend throughout the length of sheath 14.

Splitter 16 may be constructed of any of the material listed above and may be manufactured by a number of techniques including injection molding and extrusion. Splitter 16 may comprise a tube 32 that includes an inner lumen 34 (best seen in FIG. 2) adapted to slidably receive sheath 14 and a shaft coupling portion 36. According to this embodiment, shaft 12 can be secured, while sheath 14 remains slidable within lumen 34.

Splitter 16 may be used to secure the position of shaft 12 relative to y-adaptor 17. To do so, shaft 12 may be secured between two surfaces. For example, y-adaptor 17 may have a collet 38 disposed at one end. Collet 38 is essentially the same in form and function as typical known collets. When shaft 12 is disposed at coupling portion 36, a collar 40 may be tightened onto collet 38, causing collet 38 deform inwardly toward splitter 16. As collet 38 becomes more closely associated with splitter 16 (i.e., tightened onto splitter 16), shaft 12 may be secured between collet 38 and coupling portion 36.

A handle 42 may be coupled to sheath 14 near proximal end 24 thereof. Handle 42 may include a button 44 that may be configured so that actuation of button 44 may result in movement of sheath 14. For example, button 44 may be slidable along the longitudinal axis of handle 42 such that movement button 44 in a distal direction results in substantially equivalent movement of sheath 14 in the distal direction. According to this embodiment, handle 42 may be used to control the position of sheath 14. Moreover, when handle 42 is used in combination with splitter 16 such that shaft 12 may be secured relative to y-adaptor 17, handle 42 may be used to easily and precisely deliver or retrieve filter 18.

FIG. 2 is a perspective view of splitter 16. As mentioned above, splitter 16 may include tube 32 having inner lumen 34 adapted and configured to slidably receive sheath 14. Variations between different splitters appropriate for multiple embodiments may include variations of shaft coupling portion 36 as depicted in this and a number of the following figures. For example, shaft coupling portion 36 may include a lumen opening 46 to a shaft lumen 48 that extends through at least a portion of splitter 16. According to this embodiment, shaft 12 may be configured to pass through opening 46 and into shaft lumen 48.

Securing shaft 12 relative to y-adaptor 17 when using splitter 16 may occur in a number of different ways. It is believed that a portion of shaft 12 would be disposed at opening 46 that would be sufficient to allow shaft 12 to be secured between splitter 16 and collet 38 (as shown in FIG. 1). According to this embodiment, shaft 12 would pass through opening 46 (for example by back loading shaft 12 into opening 46) and into lumen 48. Collar 40 may then be actuated to secure shaft 12 between collet 38 and splitter 16. Alternatively, lumen 48 may be collapsed on shaft 12 due to pressure exerted by collet 38. According to this embodiment, collet 38 can collapse lumen 48 by actuating collar 40.

FIG. 3 is a cross-sectional view through line 3-3 of splitter 16. Shaft lumen 48 may be adapted to slidably receive shaft 12. In addition, shaft lumen 48 may include structural support for inner lumen 34 in the form of a support tube 50 (e.g., a stainless steel tube, etc.) disposed proximate at least a portion of inner lumen 34. Manufacturing of splitter 16 with support tube 50 (and other splitters and support tubes described herein) may include providing support tube 50 and overmolding or coextruding at least a portion of splitter 16 therewith. Support tube 50 may add sufficient structural support so as to prevent inner lumen 34 from collapsing on sheath 14 when securing shaft 12. Alternatively, splitter 16 may be manufactured to include a web region 51 between inner lumen 34 and shaft lumen 48 that is sufficiently large to provide any necessary structural support.

FIG. 4 is a perspective view of an alternate splitter 116. Splitter 116 may include inner lumen 134 and shaft coupling portion 136 that includes a slot 152 extending along the length of splitter 116. According to this embodiment, shaft 12 may be disposed within slot 152 and could be front loaded or be back loaded. Slot 152 may be shaped so that shaft 12 may be coupled to splitter 116 by snapping or otherwise disposing shaft 12 into slot 152. According to this embodiment, shaft 12 may be secured relative to y-adaptor 17 by snapping shaft 12 into slot 152 and tightening collet 38.

As an alternative to or in addition to what is described above, shaft 12 may be also secured by collet 38 as described above. For example, shaft 12 may be disposed within slot 152 and be secured between slot 152 and collet 38 by actuating collar 40 to tighten collet 38.

A cross-sectional view through line 5-5 of splitter 116 is depicted in FIG. 5. Similar to what is described above, splitter 116 may include structural support as described above. For example, splitter 116 may further comprise support tube 150 disposed proximate at least a portion of inner lumen 134.

FIG. 6 is a perspective view of a second alternate splitter 216. Splitter 216 includes inner lumen 234 and is essentially similar to splitter 116 except that shaft coupling portion 236 includes an alternate slot 252 having a slightly different shape than slot 152. The shape of slot 252 may simplify the process of securing shaft 12 or may provide other advantages. For example, slot 252 may be used to secure shaft 12 to splitter 216 by snapping or otherwise disposing shaft 12 into slot 252 (and, in some embodiments, tightening collet 38) in a manner similar to what is disclosed above. Alternatively, shaft 12 may be secured between splitter 216 and collet 38, for example by actuating collar 40 so as to tighten collet 38.

A cross-sectional view through line 7-7 of splitter 216 is depicted in FIG. 7. Similar to what is described above, splitter 216 may include structural support. For example, splitter 216 may further comprise a support tube 250 disposed proximate at least a portion of inner lumen 234.

FIG. 8 is a perspective view of a third alternate splitter 316. Splitter 316 includes inner lumen 334 and is similar to the previously disclosed wire locks except that shaft coupling portion 336 includes a plurality of raised ribs 354 and a plurality of slots 352 between ribs 354. Slots 352 may be adapted to receive shaft 12 in ways analogous to what is described above. For example, shaft 12 may be disposed within slots 352.

A cross-sectional view through line 9-9 of splitter 316 is depicted in FIG. 9. Similar to what is described above, splitter 316 may include structural support. For example, splitter 316 may further comprise support tube 350 disposed proximate at least a portion of inner lumen 334.

FIG. 10 is an enlarged view of a fourth alternate splitter 416. Splitter 416 includes inner lumen 434 and is essentially similar to splitter 316 except that shaft coupling portion 436 includes raised ribs 454 that are larger (i.e., define deeper slots 452 between ribs 454) than ribs 354. Slots 452 may be adapted to receive and shaft 12 in ways analogous to what is described above.

A cross-sectional view through line 11-11 of splitter 416 is depicted in FIG. 11. Similar to what is described above, splitter 416 may include structural support. For example, splitter 416 may further comprise support tube 450 disposed proximate at least a portion of inner lumen 434.

FIG. 12 is a perspective view of a fifth alternative splitter 516. Splitter 516 may include inner lumen 534, shaft coupling portion 536, opening 546, and shaft lumen 548 that may be substantially similar to any of those listed above. In addition, shaft coupling portion 536 may further comprise a physical stop 556. Physical stop 556 may make it easier for a user to determine how far splitter 516 needs to be advanced within collet 38 or prevent splitter 516 from advancing too deeply into collet 38.

As shown in FIG. 12, stop 556 is shaped as a full circumference member or enlargement coupled to splitter 516. It can be appreciated that stop 556 could be essentially any shape or configuration that is appropriate for stopping splitter 516 from advancing too deeply into collet 38. For example, stop 556 may comprise a single tab or notch, a partial circular member (similar to what is shown in FIG. 12 except not covering the full circumference of splitter 556), etc.

FIG. 13 is a perspective view of a sixth alternative splitter 616. Splitter 616 may include shaft coupling portion 636 having inner lumen 634, a plurality of ribs 654, and a luer adapter 658. Although FIG. 13 depicts shaft coupling portion 636 as having ribs 654, it should be noted that any of the shaft coupling portions discussed throughout this detailed description may be substituted without departing from the spirit of the invention. Luer adapter 658 may allow other objects to be coupled to splitter 616. For example, FIG. 14 depicts a passive valve 660 coupled to splitter 616. Passive valve 660 may prevent blood from being lost through sheath 14 (or inner lumen 634) during a medical procedure.

Figure 15:
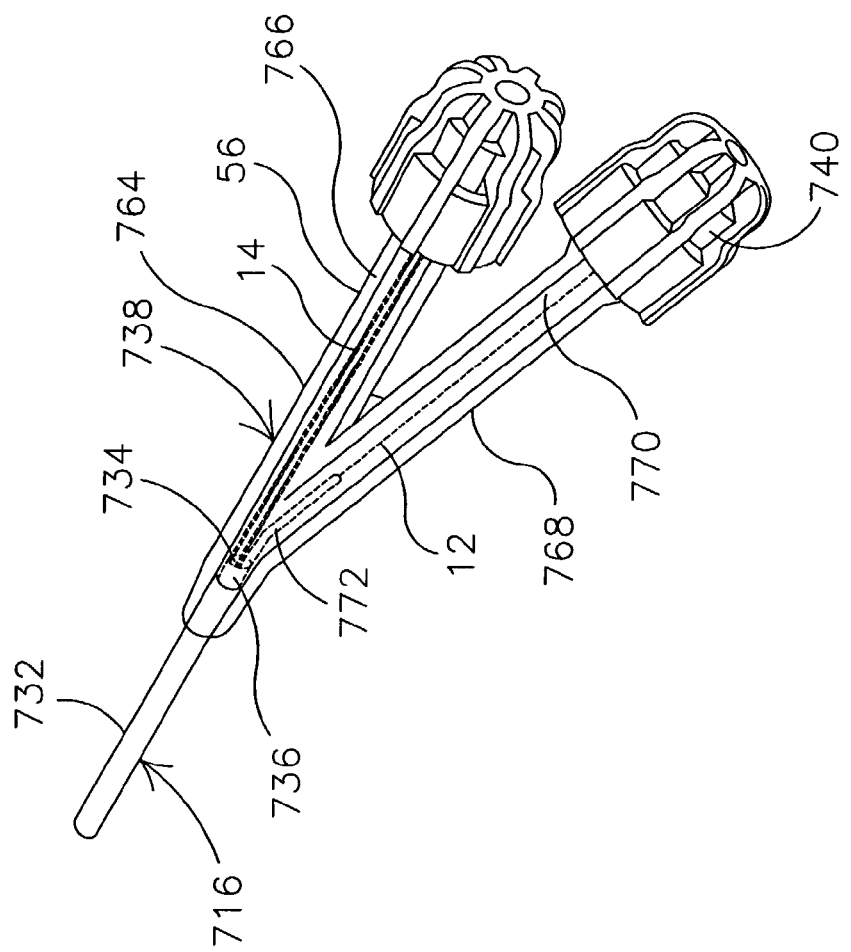
FIG. 15 is a plan view of a splitter coupled to a y-adapter according to an embodiment of the invention.

FIG. 15 is an enlarged view of a seventh alternate splitter 716. Splitter 716 may be attached to hub 15 of guide catheter 13 in place of y-adapter 17 (please refer to FIG. 1). According to this embodiment, splitter 716 may include a dual touhy y-adapter 738 having a main branch 764 having a main lumen 766. In addition, y-adapter 738 may include and a side branch 768 having a side lumen 770.

Splitter 716 may include any of the features attributed to similar objects above and may comprise tube 732, inner lumen 734, and shaft coupling portion 736. Inner lumen 734 may be in fluid communication with main lumen 766. Shaft coupling portion 736 may include a wire guide 772 that is in fluid communication with side lumen 770. According to this embodiment, shaft 12 may be disposed within wire guide 772 and may be branched away from splitter 716 and into side lumen 770.

Shaft 12 may then be secured by using locking member 740 in a manner similar to what is described above. For example, locking member 740 may comprise a collet assembly that includes a collet (similar to collet 38) that clamps down upon shaft 12 when the locking member 740 (e.g., a collar similar to collar 40) is actuated. A person of ordinary skill in the art would be familiar with uses of a collet that may be appropriate for multiple embodiments.

Figure 16:
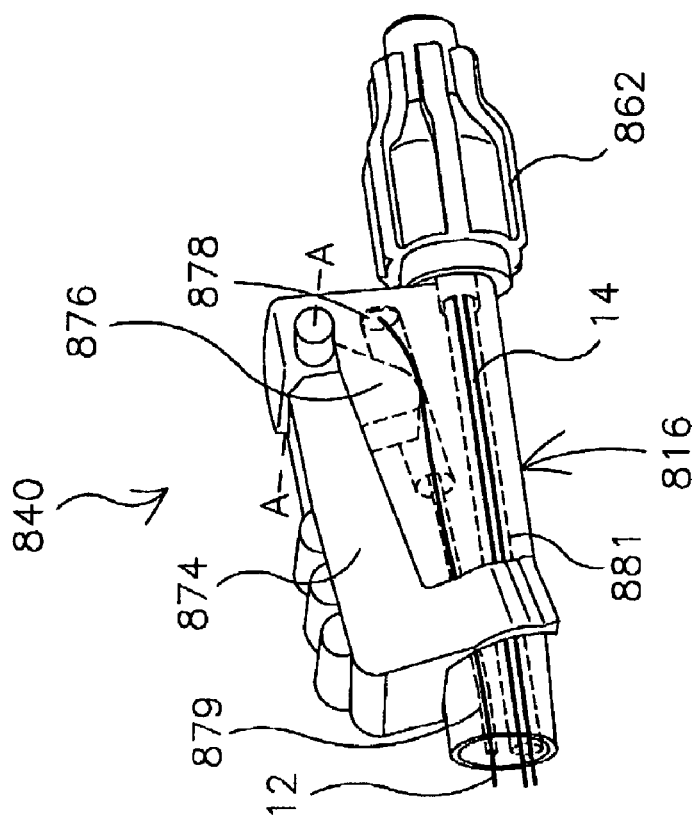
FIG. 16 is a perspective view of a locking member for securing a wire to a hub.

FIG. 16 is a perspective view of an alternate locking member 840. Locking member 840 may be used in place of y-adaptor 17 or in conjunction with (i.e., attached at one end of) y-adaptor 17, y-adaptor 738, etc. Locking member 840 may comprise a hinged arm 874 having a pinching portion 876 rotatable about an axis A. Shaft 12 may pass through a collapsible wire tube 878 such that when hinged arm 874 is clamped, pinching portion 876 applies a force onto tube 878 sufficient to collapse tube 878 and secure shaft 12 therein. Thus, tube 878 may be comprised of a compressible or collapsible material such as silicone. Shaft 12 can enter wire tube 878 by passing through a wire conduit 879 coupled to collapsible tube 878. Likewise, sheath 14 may be disposed within a sheath conduit 881. While shaft 12 is secured, sheath 14 may moved independently of shaft 12. Hinged arm 874 may be unclamped to relieve the force applied onto wire tube 878 by pinching portion 876. Locking member 840 may be manufactured by a number of techniques including injection molding.

Figure 17:
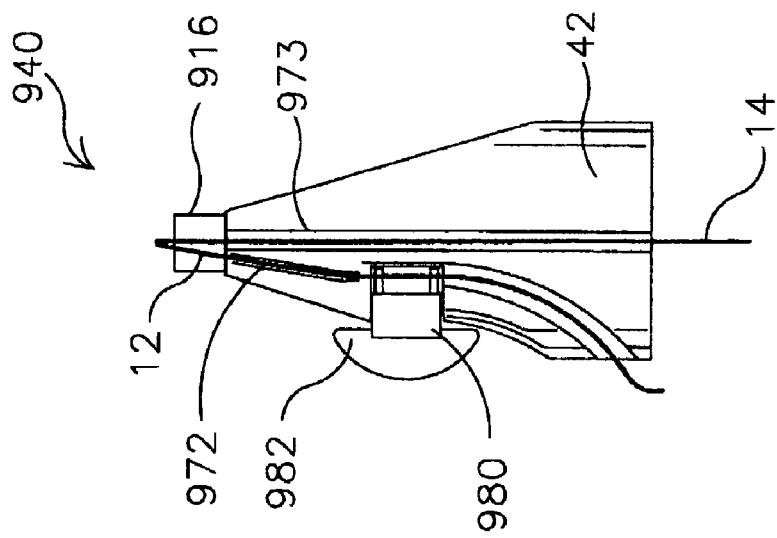
FIG. 17 is a perspective view of an alternate locking member for securing a wire to a hub.

FIG. 17 is a perspective view of a second alternate locking member 940. This embodiment may be used in conjunction with any of the shaft coupling portions described above and may be incorporated into a distal end of handle 42 (please see FIG. 1). Locking member 940 includes a splitter 916 that separates sheath 14 and shaft 12 by allowing sheath to pass into a sheath conduit 973 and shaft 12 to pass into a wire guide 972. Wire guide 972 is adapted to slidably receive to shaft 12 and a fitting 980 that may be secured to wire guide 972. A pinching button 982 may be coupled to fitting 980 such that pressing button 982 may dispose fitting 980 onto wire guide 972, securing wire 12 in position. Locking member 940 may be manufactured by a number of techniques including injection molding.

FIG. 18 is a side view of an alternate embolic protection assembly 1010 including a sliding handle 1084. Sheath 14 may be allowed to freely move within inner lumen 34 and be used with a collet 38 and collar 40 as described previously in FIG. 1 (or other analogous splitters or analogous objects described herein). Handle 1084 (an alternate to handle 42) may include means for actuating sheath 14, for example a button 1086 or equivalents thereof. By including a splitter in accordance with any of the above-described embodiments, button 1086 may be used to shift the position of sheath 14 relative to shaft 12.

Because handle 1086 may be disposed a distance away from collar 40, actuation of sheath 14 may result in bowing between handle 1084 and collar 40. Bowing may interfere with the ability of a user to shift shaft 12 relative to sheath 14. To address this issue, handle 1084 may be slidable along the length of sheath 14.

Handle 1084 may further comprise a touhy-borst fitting 1088 that may be used to secure handle 1084 to sheath 14. An intermediate shaft 1089 may extend between handle 1084 and fitting 1088 and be integrally coupled to button 1086. According to this embodiment, handle 1084 may be slid to a position proximate collar 40 when fitting 1088 is loosened. When handle 1084 is moved to a desirable position (e.g., proximate collar 40) fitting 1088 may be tightened to secure handle 1084 to sheath 14. Alternatively, fitting 1088 may comprise a collet or other element appropriate for securing handle 1084 relative to sheath 14.

Once handle 1084 is secured relative to sheath 14, sheath 14 may be manipulated relative to shaft 12 by actuating button 1086. In order to accommodate movement of sheath 14 relative to shaft 12, intermediate shaft 1089 may be moveable within a portion of handle 1084. For example, when button 1086 is actuated in the proximal direction, intermediate shaft 1089 and fitting 1088 move proximally, increasing the space between handle 1084 and fitting 1088. Because sheath 14 is secured by fitting 1088, proximal movement of fitting 1088 results in proximal movement of sheath 14. Thus, having intermediate shaft 1089 disposed movably within a portion of handle 1084 allows handle to function in order to both alter the position of sheath 14 and be slidable along sheath 14.

Figure 19:
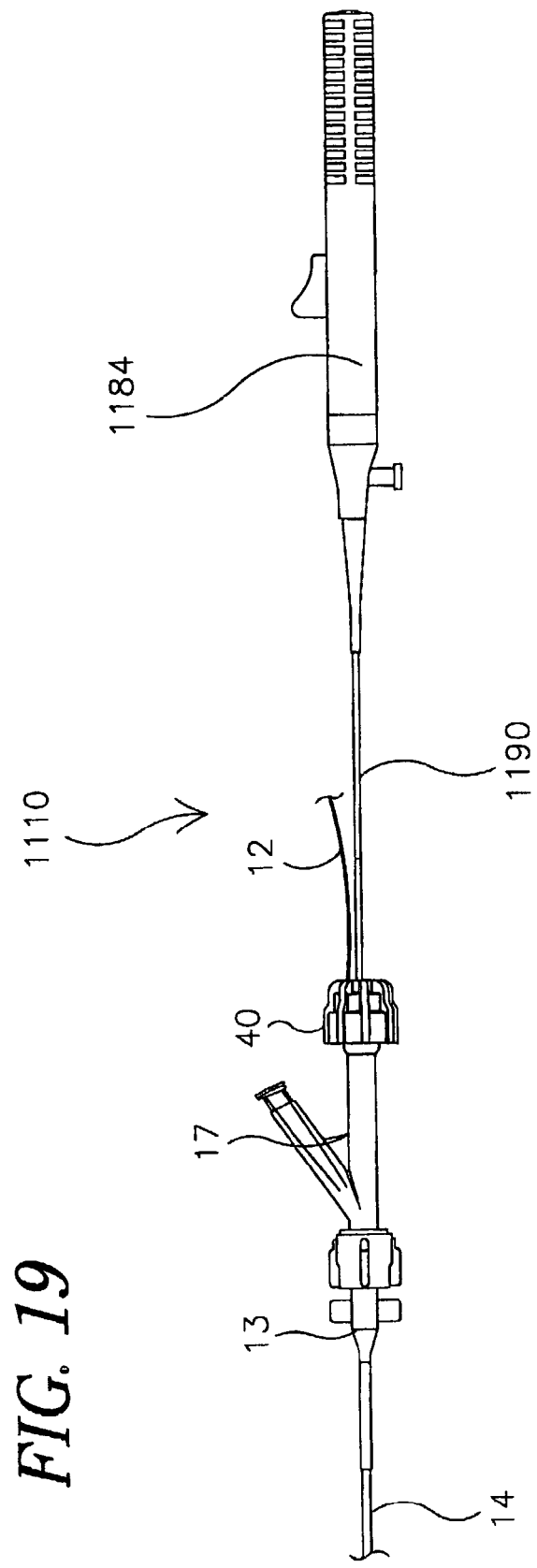
FIG. 19 is a side view of a second alternate embolic protection assembly.

FIG. 19 is a side view of a second alternate embolic protection assembly 1110 that includes a securement shaft 1190. Securement shaft 1190 is an alternative way to address catheter bowing. Securement shaft 1190 can be, for example, located between handle 1184 collar 40. Securement shaft 1190 may extend distally beyond collar 40 but should not go beyond the aortic arch when used for a medical procedure. For example, securement shaft 1190 may be about twelve to fourteen inches in length. Securment shaft 1190 may also have an outside diameter small enough to assure that it may fit into a guide catheter. Securement shaft 1190 may provide physical support in order to prevent catheter bowing. Securement shaft 1190 may also address the issue of inadvertent movement of handle 1184 while retrieving filter 18.

Securement shaft 1190 may be manufactured by extrusion. Moreover, securment shaft 1190 may further comprise an outer wire braiding that may help prevent securement shaft 1190 from collapsing due to the clamping force of a fitting (e.g., a touhy-borst fitting). In addition, it should be noted that embodiments of splitters, locking members, hubs, handles, and other elements disclosed above may also be used in combination with one another. Alternatively, features of any of the locking members disclosed above may be incorporated into handle 1184.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention.

The invention's scope is, of course, defined in the language in which the appended claims are expressed.

What is claimed is:

1. A shaft and sheath lock system comprising:
   a sheath having a proximal end, a distal end, and a lumen extending therethrough;
   a shaft having a proximal end and a distal end, wherein at least a portion of the shaft is disposed within the lumen of the sheath;
   a filter coupled to the distal end of the shaft;
   a hub assembly coupled to the sheath; and
   a splitter coupled to the hub assembly, the splitter including a tube having an inner lumen adapted to slidably receive the sheath, and a shaft coupling portion to secure the shaft relative to the hub assembly;
   wherein the sheath extends through the inner lumen through a length of the tube and the shaft extends exterior of the inner lumen along the length of the tube in which the sheath extends through the inner lumen, such that a portion of the splitter is positioned between the sheath and the shaft along the length of the tube in which the sheath extends through the inner lumen and the shaft extends exterior of the inner lumen.

2. The system in accordance with claim 1, wherein the shaft coupling portion includes a wire lumen.

3. The system in accordance with claim 1, wherein the hub assembly includes a y-adapter having a main lumen and a side lumen.

4. The system in accordance with claim 3, wherein y-adaptor includes a collet.

5. The system in accordance with claim 4, wherein the shaft may be secured relative to the hub assembly by the collet.

6. The system in accordance with claim 4, wherein a collar is coupled to the y-adapter such that tightening the collar onto the y-adaptor deforms the collet and secures the shaft relative to the hub assembly.

7. The system in accordance with claim 1, wherein the shaft may be secured relative to the hub assembly by a pinchable tube coupled to the hub assembly.

8. The system in accordance with claim 1, wherein the shaft coupling portion includes at least one slot.

9. The system in accordance with claim 8, wherein the slot is defined as the space between a plurality of raised ribs.

10. The system in accordance with claim 1, wherein the splitter further comprises a physical stop.

11. The system in accordance with claim 1, wherein the splitter includes a luer adapter.

12. The system in accordance with claim 11, further comprising a passive valve ached to the luer adapter.

13. The system in accordance with claim 1, further comprising a sliding handle.

14. The system in accordance with claim 1 further comprising a handle coupled to the sheath and a securment shaft coupled to the handle.

15. The system in accordance with claim 1, wherein the shaft coupling portion includes at least one longitudinal slot extending along the length of the tube.

16. A shaft and sheath lock system for an embolic protection device, comprising:
   a sheath having a proximal end, a distal end, and a lumen extending therethrough;
   an elongate shaft having a distal end, wherein at least a portion of the shaft is disposed within the lumen of the sheath;
   a filter coupled to the distal end of the shaft;

a y-adapter coupled to the sheath, the y-adapter having a main lumen and a side lumen;

a collet disposed at a proximal end of the main lumen;

a collar coupled to the proximal end of the main lumen; and a splitter coupled to the y-adapter at the main lumen, the splitter including a tube having an inner lumen adapted to slidably receive the sheath and a shaft coupling portion to secure the shaft relative to the y-adaptor by tightening the collar onto the y-adaptor so as to deform the collet;

wherein the sheath extends through the inner lumen through a length of the tube and the shah extends exterior of the inner lumen along the length of the tube in which the sheath extends through the inner lumen, such that a portion of the splitter is positioned between the sheath and the shaft along the length of the tube in which the sheath extends through the inner lumen and the shaft extends exterior of the inner lumen.

17. The system in accordance with claim 16, wherein the shaft coupling portion includes a wire lumen.

18. The system in accordance with claim 16, wherein the shaft coupling portion includes at least one slot.

19. The system in accordance with claim 16, wherein the slot is defined as the space between a plurality of raised ribs.

20. The system in accordance with claim 16, wherein the splitter further comprises a physical stop.

21. The system in accordance with claim 16, wherein the splitter includes a luer adapter.

22. The system in accordance with claim 21, further comprising a passive valve attached to the luer adapter.

23. The system in accordance with claim 16, wherein the hub comprises a sliding handle.

24. The system in accordance with claim 16, further comprising a handle coupled to the sheath and a securement shaft coupled to the handle.

25. The system in accordance with claim 16, wherein the shaft coupling portion includes at least one longitudinal slot extending along the length of the tube.

26. A shaft and sheath lock system comprising:

a sheath having a proximal end, a distal end, and a lumen extending therethrough;

a shaft having a proximal end and a distal end, wherein at least a portion of the shaft is disposed within the lumen of the sheath;

a filter coupled to the distal end of the shaft;

a hub assembly coupled to the sheath; and a splitter coupled to the hub assembly, the splitter including a tube having a first end, a second end, and a length between the first end and the second end, the splitter including an inner lumen adapted to slidably receive the sheath, and a shaft coupling portion to secure the shaft relative to the hub assembly;

wherein the sheath extends through the inner lumen of the splitter and the shaft extends exterior of the inner lumen over the entire length of the tube.

27. The system in accordance with claim 26, wherein the shaft extends exterior of the splitter over the entire length of the tube.

28. The system in accordance with claim 26, wherein a portion of the splitter is positioned between the sheath and the shaft along the length of the tube in which the sheath extends through the inner lumen and the shaft extends exterior of the inner lumen.

* * * * *